United States Patent [19]

Ezawa et al.

[11] Patent Number: 4,890,481
[45] Date of Patent: * Jan. 2, 1990

[54] SYSTEM FOR MEASURING FOREIGN MATERIALS IN LIQUID

[75] Inventors: Masayoshi Ezawa; Shigeru Wakana; Akira Misumi; Yoshifumi Tomita, all of Mobara; Yutaka Hiratsuka, Yokohama, all of Japan

[73] Assignee: Hitachi, Ltd., Tokyo, Japan

[*] Notice: The portion of the term of this patent subsequent to Oct. 25, 2006 has been disclaimed.

[21] Appl. No.: 226,204

[22] Filed: Jul. 29, 1988

Related U.S. Application Data

[63] Continuation of Ser. No. 14,787, Feb. 13, 1987, Pat. No. 4,779,451.

[30] Foreign Application Priority Data

Feb. 17, 1986 [JP] Japan ................................ 61-30811
Feb. 17, 1986 [JP] Japan ................................ 61-30812
Feb. 17, 1986 [JP] Japan ................................ 61-30813

[51] Int. Cl.$^4$ .......................................... G01N 15/07
[52] U.S. Cl. ................................. 73/53; 73/865.5
[58] Field of Search ............. 73/53, 61 R, 1 R, 865.5; 356/335

[56] References Cited

U.S. PATENT DOCUMENTS

| 3,320,428 | 5/1967 | Wagstaffe et al. | 73/53 |
| 3,719,090 | 3/1973 | Hathaway | 73/865.5 |
| 4,618,587 | 10/1986 | Pemoli et al. | 73/1 R |
| 4,779,451 | 10/1988 | Ezawa et al. | 73/53 |

FOREIGN PATENT DOCUMENTS 2173004 10/1986 United Kingdom .

Primary Examiner—Hezron E. Williams
Attorney, Agent, or Firm—Antonelli, Terry & Wands

[57] ABSTRACT

A system for measuring a foreign material in a liquid, includes a sampling section, vacuum deaerators, foreign material measuring sensors. The sampling section prepares a sample liquid containing various foreign materials having particles of different sizes and numbers and a calibration standard liquid containing particles of known sizes and numbers. The vacuum deaerators deaerate gases mixed in the sample and calibration standard liquids. The sensors detect the foreign materials in the deaerated liquids. These sensors are arranged in front of the deaerators, respectively.

3 Claims, 5 Drawing Sheets

SYSTEM FOR MEASURING FOREIGN MATERIALS IN LIQUID

This is a continuation division application of Ser. No. 014,787, filed Feb. 13, 1987, now U.S. Pat. No. 4,779,451.

BACKGROUND OF THE INVENTION

The present invention relates to a system for measuring foreign materials in a liquid to suitably evaluate the cleaning of components used in electron tubes and electronic devices and cleanness of these component after cleaning.

Conventional foreign material measuring apparatuses of this type are classified into an ultrasonic intermittent radiation apparatus for measuring a foreign material having a particle size of 5 to 100 $\mu$m and a laser beam radiation apparatus for measuring a foreign material having a particle size of about 0.5 to 60 $\mu$m.

The structures of these conventional measuring apparatuses are described in "On-Line Measurement of Fine Particles in Liquid" announced in the "3rd Technical Research Meeting Concerning Air Cleaning and Contamination Control" held in February, 1984.

In these conventional measuring apparatuses for measuring foreign materials, i.e., foreign materials and inorganic ions in a liquid, if bubbles, a gas, or the like is present in a liquid which is subjected to measurement and which is used for cleaning electronic components, bubbles may be attached to a surface of a sensor of the apparatus during measurements of foreign materials. In addition, the bubbles in the liquid are also subjected to measurement, and thus measurement errors are increased It is impossible to accurately measure the sizes of foreign materials and the numbers of inorganic ions and to continuously print out results or display them in a graph.

SUMMARY OF THE INVENTION

It is, therefore, a principal object of the present invention to provide a system for continuous and high precision measurement of foreign materials in a liquid subjected to measurement while bubbles in the liquid can be eliminated.

A system for measuring foreign materials in a liquid according to the present invention includes a vacuum evaporator arranged in front of a foreign material sensor for detecting a foreign material from the liquid.

The gas mixed in the liquid can be eliminated before the liquid reaches the foreign material sensor, and thus only the foreign material in the liquid can be measured.

DESCRIPTION OF THE PREFERRED EMBODIMENT

Preferred embodiments of the present invention will be described with reference to the accompanying drawings.

Figure 1:
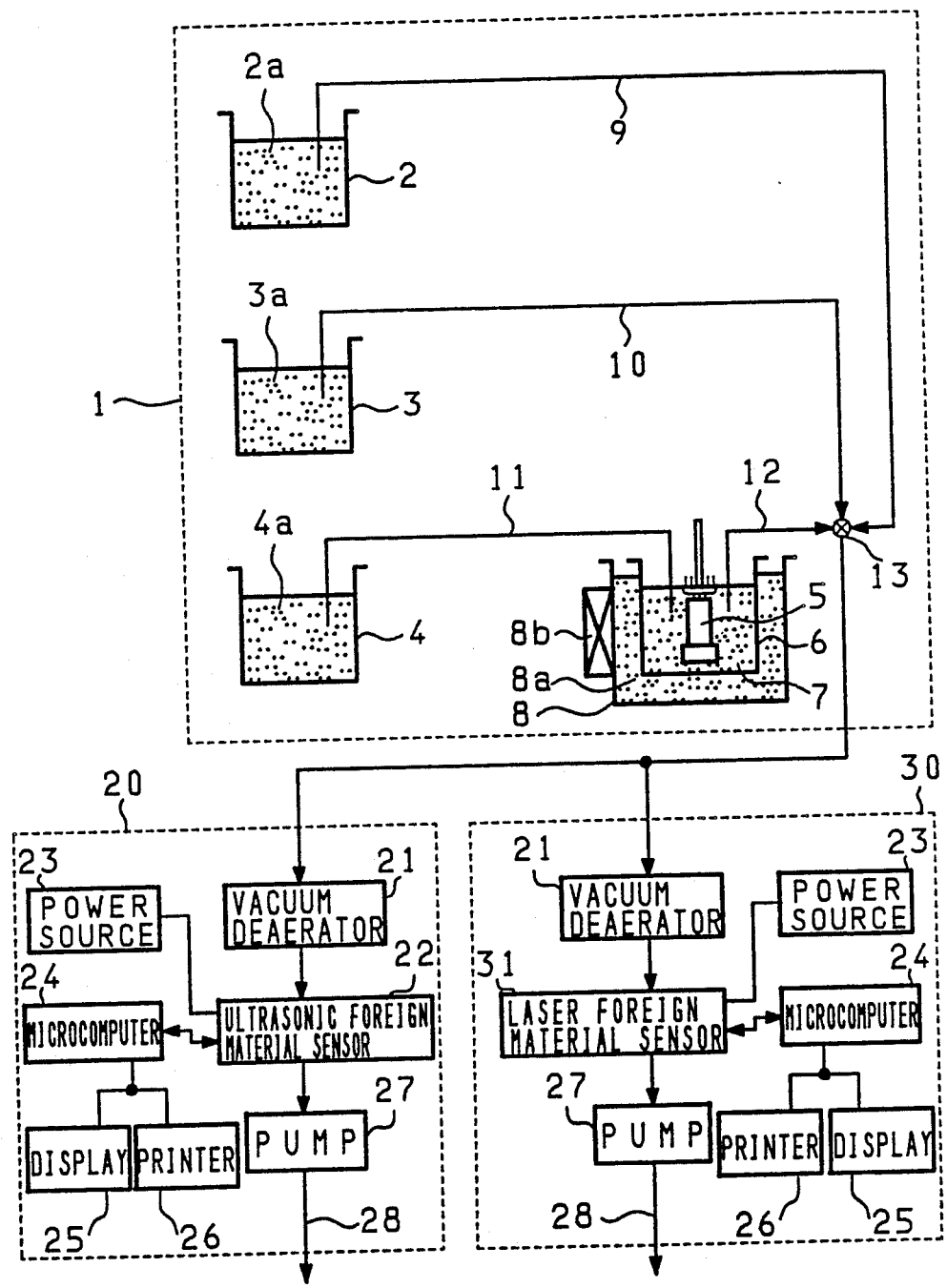
FIG. 1 is a diagram showing a system for measuring foreign materials in a liquid according to an embodiment of the present invention.

FIG. 1 shows a system for measuring foreign materials in a liquid according to an embodiment of the present invention. Referring to FIG. 1, reference numeral 1 denotes a sampling section; 2, a cleaning tank for containing a cleaning liquid 2a in which components of electron tubes and electronic devices are dipped and cleaned; 3, a standard liquid tank for storing a monitoring calibration standard liquid 3a containing a foreign material of 0.5- to 4.9-$\mu$m diameter particles at a rate of 60,000/100 ml and another foreign material of 5- to 100-$\mu$m diameter particles at a rate of 5166/100 ml; 4, a cleaning liquid tank for storing a cleaned component evaluating cleaning liquid 4a; and 5, a cleaned component. In this case, the cleaned component 5 is an electron gun assembly for a picture tube. Reference numeral 6 denotes a cleaning evaluation vessel for the cleaned component 5; 7, a liquid subjected to evaluation of the cleaned component; and 8, an ultrasonic cleaning tank which internally includes the evaluation vessel 6 and cleaning water 8a and which externally includes an ultrasonic generator 8b. Reference numeral 9 denotes a sampling tube for the cleaning liquid 2a; 10, a sampling tube for the standard liquid 3a; 11, a sampling tube for the cleaning liquid 4a; and 13, a measuring liquid selection valve for selecting one of the liquids flowing through the tubes 9, 10, and 12. These liquids are continuously flowing at a flow rate of 0.1 to 0.15 l/min.

Reference numeral 20 denotes an ultrasonic foreign material measuring section. Reference numeral 21 denotes a vacuum deaerator for deaerating a gas mixed in the liquid subjected to measurement; 22, an ultrasonic foreign material sensor for detecting a foreign material of particles each having a size of 5 to 100 $\mu$m; 23, a power source; 24, a microcomputer; 25, a display unit; 26, a printer; 27, a suction pump for draining the efluent after measurement at a flow rate of 20 to 1,000 ml/min; and 28, an efluent tube for draining the efluent from the suction pump 27.

Reference numeral 30 denotes a laser foreign material measuring section. The laser foreign material measuring section 30 includes a laser foreign material sensor 31 for detecting a foreign material having a particle size of 0.5 to 25 $\mu$m. Other components of the laser foreign material measuring section 30 are the same as those in the ultrasonic foreign material measuring section 20.

The vacuum deaerator 21 can be constituted by an organic film vacuum evaporator or a vacuum spray evaporator. In the organic film vacuum evaporator, an organic tube extends through an organic film chamber, and the chamber is evacuated. When a liquid subjected to measurement flows through the organic film chamber, the gas mixed in the liquid in the organic tube can be eliminated. In the vacuum spray evaporator, the liquid subjected to measurement is sprayed against an abutment plate at a low vacuum, and the gas is eliminated by vacuum suction. These deaerators have a function for eliminating the gas from the liquid in a concentration of 1 to 100 ppm while the liquid flows at a flow rate of 20 to 1,000 ml/min.

Figure 2A:
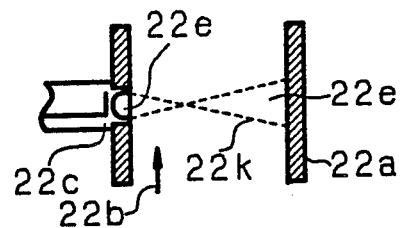
FIGS. 2A and 2B are views for explaining an ultrasonic foreign material sensor.
Figure 2B:
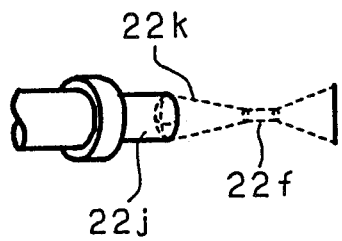
Figure 2C:
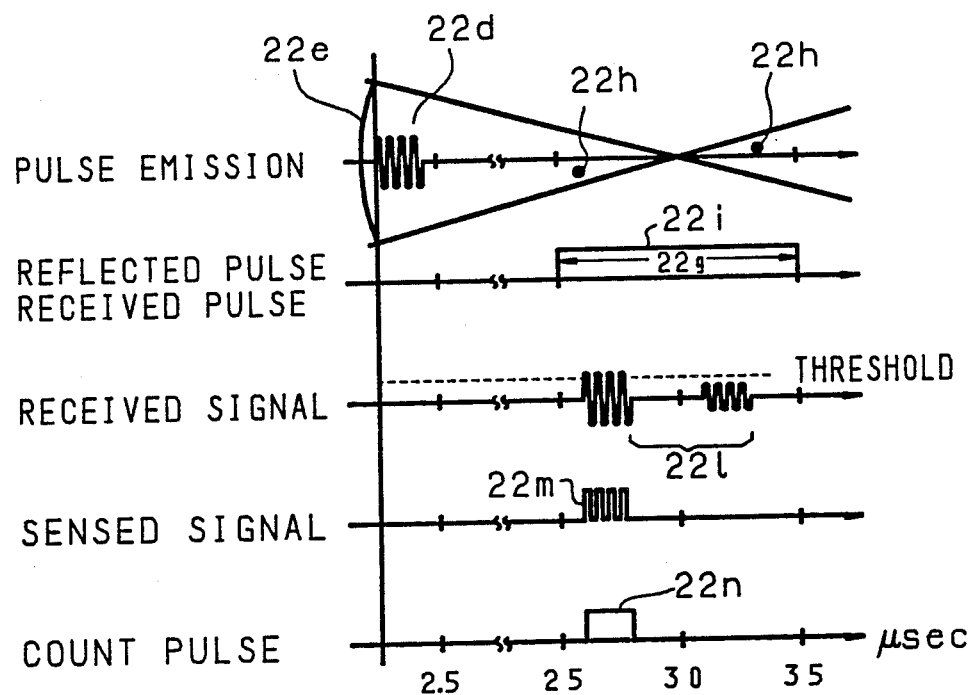
FIG. 2C is a timing chart of the operation of the ultrasonic foreign material sensor shown in FIGS. 2A and 2B.

Ultrasonic pulses 22d from the ultrasonic foreign material sensor 22 repeatedly impinge on the side surface of the flow path of the liquid 22b continuously flowing through the tube 22a at a rate of 200 pulses/sec (2 μsec/pulse), as shown in FIGS. 2A to 2C. These ultrasonic pulses 22d are obtained by converting an RF voltage of about 400 V applied to a quartz crystal element 22c into a 15-MHz ultrasonic sound pressure signal. Ultrasonic energy is focused by an acoustic lens 22e to form a conical beam, and the ultrasonic wave then propagates in the liquid 22b. By utilizing energy (proportional to the particle size) of the beam reflected by a foreign material 22h in areas 22f and 22g having the highest ultrasonic beam density, each wave reflected by each particle is detected as an echo signal. The reflected beam within only a reflected pulse reception gate 22i having a diameter of about 1.4 mm is received by a sensor 2j. Reference numeral 22k denotes an ultrasonic beam. Values 22l, 22m, and 22n of the reflected pulses in response to 1000 transmission pulses 22d are converted into counts, thereby continuously measuring foreign materials having a particle size of 5 to 100 μm.

Figure 3:
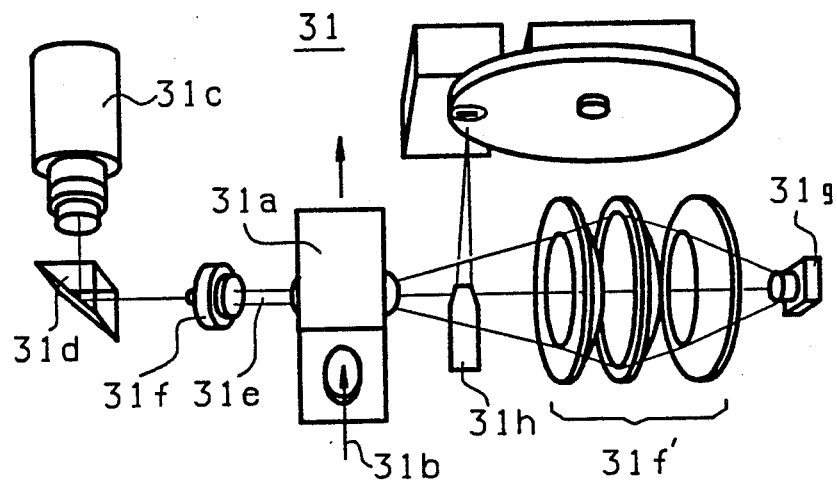
FIG. 3 is a perspective view for explaining a laser beam foreign material sensor.

In the laser foreign material sensor 31, as shown in FIG. 3, an He-Ne laser 31c is reflected by a prism 31d and focused by a focusing lens 31f. A focused laser beam 31e impinges on the side surface of a sensor cell 31a in which a liquid 31b continuously flows. Light scattered by foreign material (particle size of 0.5 to 60 μm) in the liquid 31b is focused by the focusing lens 31f, and the size and number of paticules are detected by a high-sensitivity photodiode 31g. Therefore, the particles having a size of 0.5 to 25 μm can be continuously measured. It should be noted that scattered light is reflected by a prism 31h and is not incident on the photodiode 31g.

With the above arrangement, a component (i.e., a noncleaned member represented by the component 5) such as an electron gun assembly for a picture tube is dipped and washed in distilled water in the cleaning tank 2. In this case, the distilled water is converted into the cleaning liquid 2a containing the foreign materials which have different particle sizes and had attached to the surface of the component. The cleaned component 5 is placed in the evaluation vessel 6. The cleaning liquid 4a such as distilled water is supplied from the cleaning liquid tank 4 through the sampling tube 11 to the evaluation vessel 6. An ultrasonic beam from the ultrasonic generator 8b is continuously emitted onto the component so that the component is cleaned again. Foreign materials left on the cleaned component 5 are further removed. The cleaning liquid 4a is thus converted into the liquid 7 subjected to measurement of the cleaned component. The liquid 7 and the monitoring calibration standard liquid 3a through the sampling tubes 12 and 10 are selected by the selection valve 13. The selected liquid is supplied to the vacuum deaerators 21 by the suction pumps 27 in the ultrasonic foreign measuring section 20 and the laser foreign material measuring section 30 at a rate of 100 ml/min. The bubbles and gases mixed in the liquids 7 and 3a are eliminated. In the ultrasonic foreign material measuring section 20, the liquids 7 and 3a are supplied to the ultrasonic foreign material sensor 22. As described with reference to FIG. 2, only the foreign material having a particle size of 5 to 100 μm in the liquid are measured. In the laser foreign material measuring section 30, the deaerated liquid 7 subjected to measurement and the standard liquid 3a are supplied to the laser foreign material sensor 31. As described with reference to FIG. 3, only the foreign material having a particle size of 0.5 to 4.9 μm was measured. As a result, the standard liquid 3a is measured within ±15% of the variation coefficient with respect to the standard values (i.e., 0.5- to 4.9-μm diameter particles at a rate of 60,000/100 ml, and 5- to 100-μm diameter particles at a rate of 5166/100 ml). At the same time, when the component is washed at a rate of 0.1 to 0.15 l/min, the number of foreign particles in the liquid 7 subjected to measurement for the cleaned component in the evaluation vessel 6 was 13,000 to 16,000/100 ml. 10 component samples were cleaned in only the first cleaning tank 2 without being washed with an ultrasonic wave in the evaluation vessel 6 in the sampling section 1. The samples were measured through the vacuum deaerator 21 in the ultrasonic foreign measuring section 20. In this case, a total number of foreign particles having a particle size of 5 to 100 μm was 30,000 to 50,000/sample ($\overline{X}$=46,000/sample). However, according to this embodiment, when the samples were cleaned with an ultrasonic beam again in the evaluation vessel 6, the number of foreign particles was 3,100 to 6,200/sample ($\overline{X}$=3,700/sample). Therefore, continuous foreign material measurement can be performed. When the foreign materials in the liquid are continuously measured using the vacuum deaerator 21, a sample having a known number of foreign particles and a known particle size is used, and a characteristic curve representing the relationship between ultrasonic reflection energy and the size and number of foreign particles is prepared. The prepared characteristic curve is stored in the microcomputer 24. The values of the foreign materials in the liquid, which are measured by the ultrasonic sensor 22, are calculated, and the calculated size and number of foreign particles are displayed in a graph. At the same time, the results are printed out at the printer 26 and are displayed at the display unit 25, thereby allowing continuous measurement of the foreign materials in the liquid.

Figure 4:
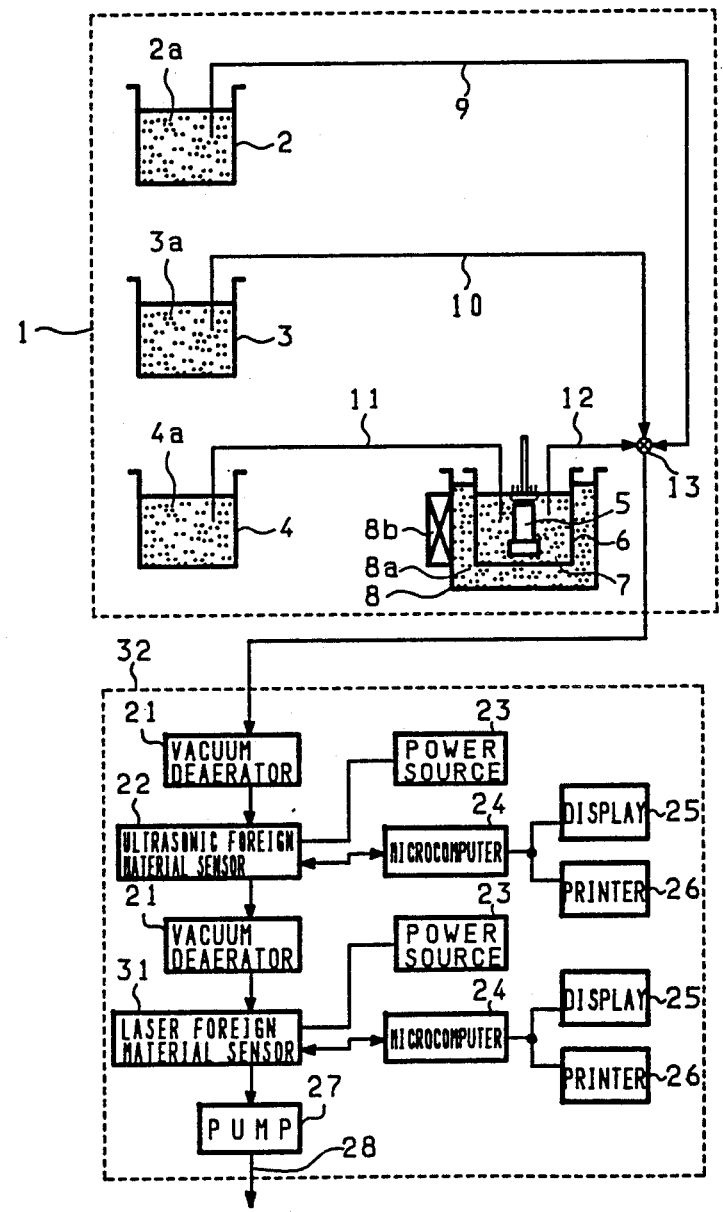
FIGS. 4 and 5 are diagrams for explaining other embodiments of the present invention.

In the above embodiment, the ultrasonic foreign material measuring section 20 and the laser foreign material measuring section 30 are connected in parallel with the sampling section 1. However, the present invention is not limited to this arrangement. As shown in FIG. 4, the ultrasonic and laser foreign material measuring sections may be connected in series with each other to constitute an ultrasonic/laser foreign material measuring section 40 to obtain the same effect as in the above embodiment. In this case, one suction pump 27 can be omitted, thereby reducing the system cost.

The vacuum deaerator may comprise a vacuum chamber having a spiral synthetic resin tube therein, a pressure sensor for maintaining a predetermined vacuum in the vacuum chamber, a control box, and a vacuum device comprising a vacuum pump.

Figure 5:
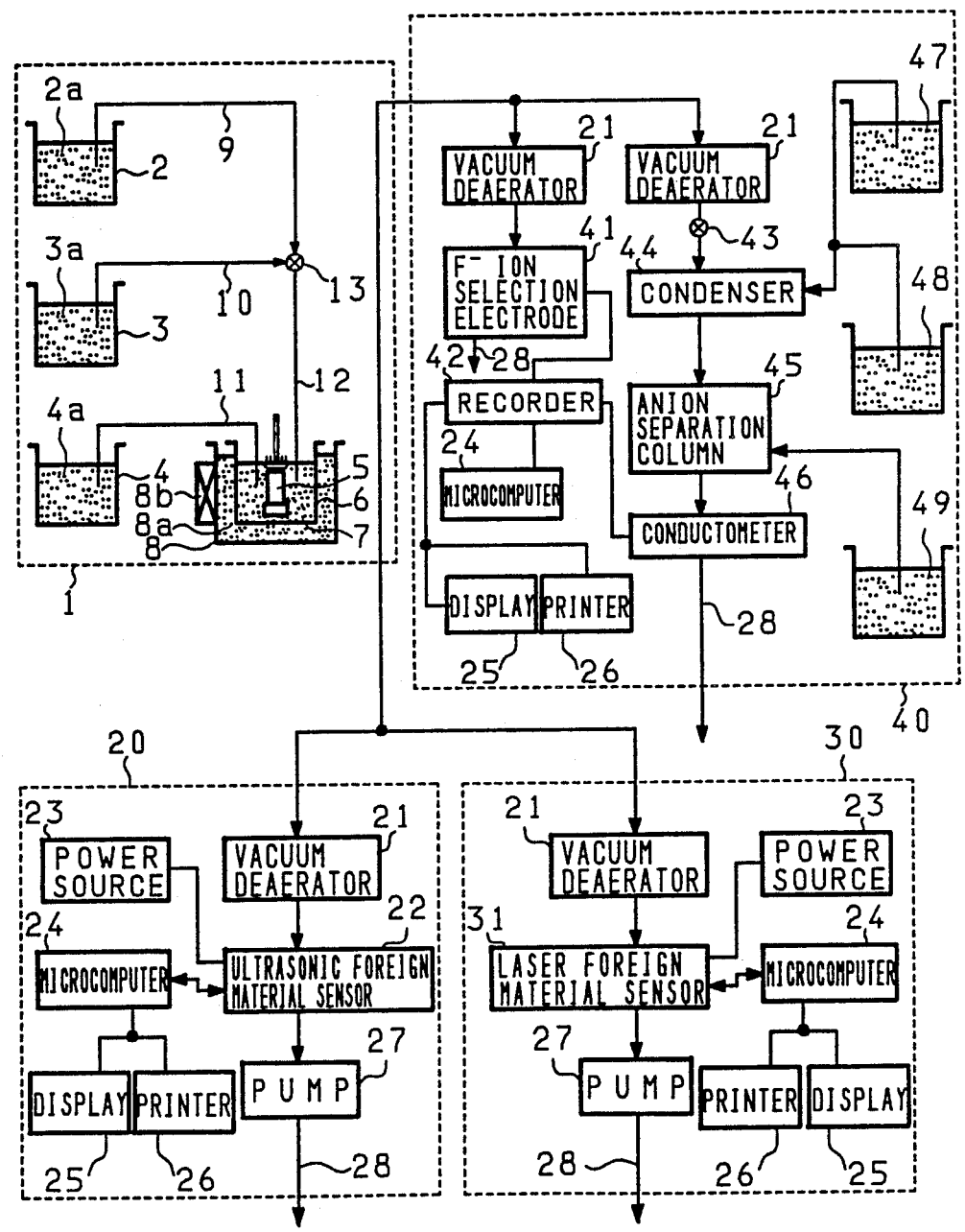

FIG. 5 shows a system for measuring foreign materials in a liquid according to still another embodiment of the present invention. The same reference numerals as in FIGS. 1 to 4 denote the same parts in FIG. 5, and a detailed description thereof will be omitted. Referring to FIG. 5, reference numeral 40 denotes an inorganic ion measuring section. Reference numeral 41 denotes an $F^-$ ion selection electrode; 42, a recorder; 43, a valve for selecting a liquid subjected to measurement; 44, a condenser having two condensing columns filled with an ion exchange resin; 45, an anion separation column; 46, a conductometer; 47, a standard liquid; 48, an anion ion eluent as a mixing solution of sodium carbonate and sodium bicarbonate; and 49, a regeneration solution such as diluted sulfuric acid used for regenerating the ion exchange resin. Other arrangements of this system are the same as those of the foreign material measuring sections 20 and 30.

With the above arrangement, a liquid 7 subjected to measurement for a cleaned component and a monitoring calibration standard liquid 3a, all of which are selected by a solution measurement selection valve 13, are selectively supplied to the inorganic ion measuring section 40. The bubbles and gases mixed in the liquid are removed by the vacuum deaerator 21. Only $F^-$ ions are selectively detected by the $F^-$ ion selection electrode 41, and an output voltage representing a value proportional to the content of $F^-$ ions is counted. The output voltage is used to measure the number of $F^-$ ions with reference to a prepared detection value. The liquid 7 deaerated by the vacuum deaerator 21 is supplied upon operation of the selection valve 43 and is condensed and eluted by the condenser 44. In the elution process, the anion ion eluent 48 is added to one condensation column in the condenser 44, and the liquid 7 is condensed in the other condensation column. The liquid 7 is sequentially separated into anions and cations. The regeneration solution 49 is added to the liquid 7 in the anion separation column 45 to separate only cations. Therefore, ions are sequentially eluted in an order of $Cl^-$, $PO_4^{---}$, $NO_3^-$, and $SO_4^{--}$. These ions can be continuously and quantitatively measured by using detection lines prepared such that the conductivities of these ions are measured beforehand and the relationship between the concentration and the conductivity of each ion is established. When the ions $Cl^-$, $F^-$, $NO_3^-$, $SO_4^{--}$, and $PO_4^{---}$ were measured, their concentrations were 5 ppm, 1 ppm, 1 ppm or less, 2 ppm, and 1 ppm or less, respectively.

When the foreign materials and the inorganic ions are continuously measured using the vacuum deaerator 21, a sample having the known number and size of foreign particles is used, and a characteristic curve representing the relationship between the energy of the reflected beam and the size and number of foreign particles. The names and conductivities of the ions are stored in the microcomputer 24. The foreign materials and the inorganic ions in the liquid subjected to measurements are respectively measured by the foreign material sensor and the inorganic ions sensor, and the measured values are calculated and plotted in a graph on the basis of the number and size of foreign particles and the contents of the inorganic ions. At the same time, the calculated values are printed out at the printer 26 and displayed at the display unit 25. Therefore, the foreign materials and the inorganic ions can be continuously measured.

According to the above embodiment, the inorganic ions and the foreign particles having a particle size up to 100 μm, both of which are mixed in the liquid subjected to measurement, can be continuously and accurately measured without being influenced by the gas mixed in the liquid. Therefore, cleanness of the cleaned components can be quantitatively evaluated. Many practical advantages can be obtained, such that an improvement of cleanness allows an improvement in product quality.

According to the above embodiments described above, the vacuum deaerating means is arranged in front of the foreign material sensor for detecting foreign materials in a liquid. Therefore, the gas mixed in the liquid can be accurately eliminated, and only the foreign materials in the liquid can be measured. Therefore, many advantages can be obtained such that the size and foreign particles as well as the inorganic ions can be continuously and accurately measured and that components having a smaller number of foreign particles attached can be continuously obtained.

What is claimed is:

1. A system for measuring a foreign material in a liquid, comprising:
sampling means for preparing a sample liquid containing various foreign materials having particles of different sizes and numbers and a calibration standard liquid containing particles of known sizes and numbers;
vacuum deaerating means for deaerating gases mixed in the sample and calibration standard liquids; and
foreign material measuring means for detecting the foreign materials in the deaerated liquids.

2. A system according to claim 1, wherein each of said vacuum deaerating means comprises one of an organic film vacuum deaerator, a vacuum spray deaerator, and a combination of a vacuum chamber and a vacuum device.

3. A system according to claim 2, wherein each of said vacuum deaerating means deaerates 1 to 100 ppm of a gas flow supplied at a rate of 20 to 1000 ml/min.

* * * * *